US008063241B2

(12) United States Patent
Lorenz et al.

(10) Patent No.: US 8,063,241 B2
(45) Date of Patent: Nov. 22, 2011

(54) PROCESS FOR THE PREPARATION OF TOLUENE-DIISOCYANATE

(75) Inventors: Wolfgang Lorenz, Dormagen (DE); Lars Padeken, Dusseldorf (DE); Bernd Pennemann, Bergisch Gladbach (DE); Friedhelm Steffens, Leverkusen (DE); Lothar Weismantel, Bergisch Gladbach (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/894,290

(22) Filed: Sep. 30, 2010

(65) Prior Publication Data

US 2011/0021811 A1    Jan. 27, 2011

Related U.S. Application Data

(63) Continuation of application No. 12/001,905, filed on Dec. 13, 2007, now abandoned.

(30) Foreign Application Priority Data

Dec. 18, 2006   (DE) .......................... 10 2006 060 181

(51) Int. Cl.
 *C07C 263/00* (2006.01)
 *C07C 249/00* (2006.01)
(52) U.S. Cl. ....................................... 560/347; 560/352
(58) Field of Classification Search .................. 560/347, 560/352
See application file for complete search history.

(56) References Cited

U.S. PATENT DOCUMENTS

| 3,128,310 A | 4/1964 | Koch |
| 3,225,094 A | 12/1965 | Wolf |
| 3,331,878 A | 7/1967 | Horn et al. |
| 3,499,035 A | 3/1970 | Kober |
| 3,626,030 A | 12/1971 | Wolters |
| 3,694,323 A | 9/1972 | Cooper et al. |
| 4,091,009 A | 5/1978 | Cassata |
| 4,137,226 A | 1/1979 | Brodsky |
| 4,654,443 A | 3/1987 | Marks et al. |
| 5,354,432 A | 10/1994 | Ambas et al. |
| 5,424,386 A | 6/1995 | Gebauer et al. |
| 5,446,196 A | 8/1995 | Benedix et al. |
| 5,468,783 A | 11/1995 | Gebauer et al. |
| 5,902,459 A | 5/1999 | Gagnon et al. |
| 6,255,529 B1 | 7/2001 | Nagase et al. |
| 6,429,336 B2 | 8/2002 | Dai et al. |
| 6,630,517 B2 | 10/2003 | Nishida et al. |
| 6,673,960 B1 | 1/2004 | Schwarz et al. |
| 2002/0010369 A1 | 1/2002 | Dai et al. |
| 2004/0118672 A1* | 6/2004 | Grun et al. ....................... 203/29 |
| 2007/0299279 A1* | 12/2007 | Pohl et al. ....................... 560/347 |

FOREIGN PATENT DOCUMENTS

| DE | 2703313 | 8/1978 |
| GB | 795639 | 5/1958 |
| WO | 2004108656 | 12/2004 |

* cited by examiner

*Primary Examiner* — Jafar Parsa
(74) *Attorney, Agent, or Firm* — N. Denise Brown; Noland J. Cheung

(57) ABSTRACT

The present invention relates to a process for the preparation of toluene-diisocyanate. In this process, toluenediamine is reacted with phosgene to give crude toluene-diisocyanate, the crude toluene-diisocyanate is purified by distillation, the distillation residue formed during the distillation is hydrolysed at temperatures of less than 230° C. under absolute pressures of less than 30 bar, and the toluenediamine formed by this process is subsequently recycled into the reaction of toluenediamine and phosgene.

10 Claims, No Drawings

PROCESS FOR THE PREPARATION OF TOLUENE-DIISOCYANATE

CROSS-REFERENCE TO RELATED PATENT APPLICATIONS

The present application is a continuation application of U.S. application Ser. No. 12/001,905, filed on Dec. 13, 2007 now abandoned, which is commonly assigned. The present application claims the right of priority under 35 U.S.C. §119 (a)-(d) of German Patent Application No. 10 2006 060 181.5, filed Dec. 18, 2006.

BACKGROUND OF THE INVENTION

The present invention relates to a process for the preparation of toluene-diisocyanate (TDI) in which toluenediamine (TDA) is reacted with phosgene to give TDI, the resultant TDI is purified by distillation, and the distillation residue formed during the distillation is hydrolysed at temperatures of less than 230° C. under absolute pressures of less than 30 bar, and the resultant TDA from this procedure is subsequently recycled into the reaction of TDA and phosgene.

The preparation of TDI by phosgenation of TDA and the subsequent purification of the crude TDI by distillation are generally known. All the known processes for the purification of crude TDI by distillation have the common feature that, in addition to the desired purified TDI, a distillation residue which must be further treated is formed by the distillation.

The known prior art describes various processes for treatment of the distillation residue which is formed in the preparation of TDI. In general, the treatment of the residue aims to maximize the yield of TDI, minimize the amount of residue which is formed, and as much as possible, provide an appropriate inexpensive and simple use for the amount of distillation residue which can no longer be used in the TDI preparation process.

The following processes are known in principle:

The mixture of isocyanate product and distillation residue can, in principle, be burned either continuously or discontinuously. The process is technically simple and can be employed for generation of service steam if a facility or installation for thermal utilization suitable for this purpose exists in the general vicinity of the isocyanate production facility of installation, in order to ensure disposal via a pipeline connection. The great disadvantage of this process, however, is the loss in yield of product which is caused by combustion of product isocyanate. Since the TDI-free or approximately TDI-free distillation residue is solid, a combustion process such as this requires that some of the TDI product be present to produce a flowable stream of material to the combustion facility.

To minimize the loss in isocyanate yield, a mixture of TDI and the distillation residue can be transferred into a stirred and heated container, and mixed with high-boiling hydrocarbons (preferably bitumen) which are inert under the distillation conditions, in order to completely distill off the free isocyanate (or as much as is reasonably possible) that is present in the residue. The remaining residue can be discharged as a flowable solid and fed to a combustion facility. Disadvantages of this process include an additional step and the use of a substance foreign to the process (e.g. bitumen), and the more involved handling of the residue product as a solid (as disclosed in EP 0548685 A2).

A further process for separating off the TDI residue is characterized by the use of kneader dryers as described in U.S. Pat. No. 5,446,196. In this process, the heated and stirred containers described above are replaced by kneader dryers. By using, for example, bitumen, the residue which remains is obtained as a flowable solid, as described in the abovementioned example, which can be employed as a fuel in, for example, cement works. The advantage of this process over the above described process is an increase in the yield of TDI, but the higher investment costs required due to the more involved technique can be regarded as a disadvantage.

Processes in which TDI distillation residues are reacted with reactants other than water in order to obtain, in addition to the amine employed in the phosgenation, valuable substances which can also be used industrially, such as, for example, the reaction of TDI residue with alkanolamine (sec U.S. Pat. No. 5,902,459) or with MDI (see DE-A-4211774, and U.S. Pat. No. 3,694,323), are also known and described in the patent literature.

The hydrolysis of isocyanate distillation residues, and particularly in the preparation of TDI, is a field which has been addressed for a relatively long time. The hydrolysis of isocyanate distillation residues is described in, for example, U.S. Pat. No. 3,128,310, U.S. Pat. No. 3,331,876, GB 795,639 and DE 2703313 A1.

In these processes, liquid or solid TDI distillation residue is hydrolysed with water under increased pressure at elevated temperature. During this procedure, some of the residue is converted into the original amine, in this case TDA, which can be recycled back into the phosgenation process after appropriate working up, and therefore, in principle, leads to an increase in the yield of TDI and a minimization of the residue. In some cases, bases such as ammonia, the original amine employed and also alkali metal hydroxide, are employed to accelerate the reaction. The process can also be conducted in two stages, in this case with the use of the original amine and water (as described in U.S. Pat. No. 4,654,443). The use of steam in the hydrolysis of solid residue is also described, with temperatures of up to 400° C. being claimed (see U.S. Pat. No. 3,225,094). Acid hydrolysis of distillation residues with subsequent drying and partial phosgenation to give the desired isocyanate is described in U.S. Pat. No. 3,636,030. WO 2004/108656 A1 describes the processing of solid TDI distillation residue, which is pulverized, suspended in water and reacted with alkali metal hydroxides, or carbonates, under pressure of 40 to 250 bar at temperatures of 200 to 370° C. The intermediate step of handling of a solid causes difficulty in a continuous TDI process and therefore seems to be a disadvantage here.

Multi-stage and therefore technically involved processes, or the handling of solid residues are also necessary as described in the processes of U.S. Pat. No. 3,499,035, U.S. Pat. No. 4,091,009 and U.S. Pat. No. 4,137,266. DE 19827086 A1 discloses a hydrolysis process for recovery of TDA from TDI distillation residue in a continuous flow, back-mixed reactor in the presence of hydrolysis product. Back-mixed reactors which are mentioned are stirred tanks, cascades of stirred tanks, a reaction mixing pump, a pumping circulation with a static mixer and/or two-component mixing nozzle, a jet loop reactor or a jet nozzle reactor. The reaction is carried out under 1 to 50 bar at temperatures of 120 to 250° C. The amine obtained from the hydrolysis is in turn fed to the phosgenation. A device and a process, inter alia, for hydrolysing TDI distillation residue and recycling the toluenediamine recovered into the phosgenation process are claimed in U.S. Pat. No. 6,630,517. The hydrolysis with pure water is described under a reactor pressure of 30 to 300 bar at a reaction temperature of 190 to 370° C. Working up of the reaction mixture is carried out successively by devolatilization (i.e. separating off of the carbon dioxide formed), dehydration and separation of the product obtained by the hydrolysis (in this case TDA) by distillation under reduced pressure. The reaction component comprises one or more tubular reactors. The hydrolysis of, inter alia, TDI distillation residue with water in a continuous process is likewise described in a tubular reactor in U.S. Pat. No. 6,255,529. The reaction conditions are stated as 100° C. or higher under 5.0 bar or higher, and the hydrolysing agent is water.

However, disadvantages of the processes mentioned above are the sometimes high expenditure in working up of the residue, the high loss in yield and the high consumption of energy required, which inter alia is caused by high pressures and temperatures during the hydrolysis.

In view of the prior art, there is a need to provide a process for the preparation of TDI in the integrated system of nitration of toluene, preparation of TDA, phosgenation of TDA, working up of TDI and recycling of chlorine, in which the highest possible yield of TDI can be achieved and the production of residual substances which have to be disposed of is minimized.

It has now been found that this aim can be achieved by employing a hydrolysis of the TDI distillation residue, and that the distillation residue of the TDI working up, in a mixture with TDI, already hydrolyses with water below a reaction pressure of 30 bar at a temperature of less than 230° C., optionally with the addition of a base, to give TDA in good yields. This TDA can be fed back to the phosgenation process.

SUMMARY OF THE INVENTION

It was an object of the present invention to provide a simple process for the preparation of TDI, in which the expenditure in the working up of the residue and the energy consumption required are minimized, while simultaneously minimizing the loss in yield of TDI and the production of residual substances which have to be disposed off.

The invention relates to a process for the preparation of toluene-diisocyanate, which comprises
  a) reacting toluenediamine with phosgene to form crude toluene-diisocyanate,
  b) purifying the crude toluene-diisocyanate by distillation, thus forming purified toluene-diisocyanate and a mixture containing toluene-diisocyanate and the distillation residue of toluene-diisocyanate,
  c) continuously mixing the mixture containing toluene-diisocyanate and the distillation residue of toluene-diisocyanate with water, at a temperature of less than 230° C. under an absolute pressure of less than 30 bar, and allowing said mixture to react under the same conditions (i.e. at a temperature of less than 230° C. under an absolute pressure of less than 30 bar), in one or more tubular reactors connected in series, to form toluenediamine,
  d) optionally purifying the resultant toluenediamine from step c), and
  e) recycling at least a portion of said toluenediamine into the reaction in step a).

DETAILED DESCRIPTION OF THE INVENTION

The reaction of TDA with phosgene is known in principle and is described in, for example, Ullmann's Encyclopedia of Industrial Chemistry, 5th ed. Vol. A 19 p. 390 et seq., VCH Verlagsgesellschaft mbH, Weinheim, 1991; and G. Oertel (ed.) Polyurethane Handbook, 2nd edition, Hamer Verlag, Munich, 1993, p. 60 et seq.; and G. Wegener et al. Applied Catalysis A: General 221 (2001), p. 303-335, Elsevier Science B.V.

In accordance with the present invention, the reaction of TDA and phosgene in step a) preferably takes place as follows:

TDI is prepared by reacting TDA with phosgene in process step a). The TDA preferably originates from the hydrogenation of dinitrotoluene (DNT). Process step a) is also called phosgenation herein. The phosgenation reaction takes place with the formation of hydrogen chloride as a by-product.

The synthesis of isocyanates in general, and of TDI in particular, is known adequately from the prior art, and as a rule, phosgene is employed in a stoichiometric excess, based on the quantity of TDA. The phosgenation in step a) conventionally takes place in the liquid phase as is disclosed in, for example, DE 3744001 C1 and EP 0314985 A1, which are believed to correspond to U.S. Pat. No. 5,117,048 and U.S. Pat. No. 4,851,570, respectively, the disclosures of which are hereby incorporated by reference, with it being possible for the phosgene and TDA to be dissolved in a solvent. Preferred solvents are chlorinated aromatic hydrocarbons such as, for example, chlorobenzene, o-dichlorobenzene, p-dichlorobenzene, trichlorobenzenes, the corresponding chlorotoluene or chloroxylenes, chloroethylbenzene, monochlorodiphenyl, α- and β-naphthyl chloride, benzoic acid ethyl ester, phthalic acid dialkyl esters, diisodiethyl phthalate, toluene and xylenes. Additional examples of suitable solvents are known and described in the prior art. As is moreover known from the prior art, e.g. in WO-A-96/16028 which is believed to correspond to U.S. Pat. No. 5,925,783, the disclosure of which is hereby incorporated by reference, the isocyanate formed can also function as a solvent for the phosgene. In another, preferred embodiment, the phosgenation takes place above the boiling point of the TDA. Gas phase phosgenation is described in, for example, EP 570 799 A, EP 1555258 A1, EP 1526129 A 1 or DE 10161384 A1, which are believed to correspond to U.S. Pat. No. 5,449,818, U.S. Pat. No. 6,930, 199, U.S. Published Patent Application 2005/0113601 or U.S. Pat. No. 7,019,164, respectively, the disclosures of which are hereby incorporated by reference. Advantages of this process over the otherwise conventional liquid phase phosgenation lie in the saving in energy due to the minimization of an involved solvent and phosgene circulation.

The TDA can be reacted with phosgene in a one-stage or two-stage, or optionally, a multi-stage reaction. In this context, both a continuous and a discontinuous operating procedure are possible.

If a one-stage phosgenation in the gas phase is chosen, the reaction is carried out above the boiling temperature of TDA. Preferably the reaction is carried out within an average contact time of from 0.05 to 5 seconds, at temperatures of from 200° C. to 600° C. as is described in DE 10161384 A1, which is believed to correspond to U.S. Pat. No. 7,019,164, the disclosure of which is hereby incorporated by reference.

Temperatures of from 20° C. to 240° C. and pressures of from 1 bar to approx. 50 bar are conventionally employed in the phosgenation in the liquid phase as disclosed in U.S. Pat. No. 3,544,611, the disclosure of which is hereby incorporated by reference. The phosgenation in the liquid phase can be carried out in one stage or several stages, with it being possible for phosgene to be employed in a stoichiometric excess. In this context, the TDA solution and the phosgene solution are preferably combined via a static mixing element and then led, for example, from the bottom upwards through one or more reaction towers, where the mixture reacts to yield the desired isocyanate. In addition to reaction towers provided with suitable mixing elements, reaction containers with a stirring device can also be employed. Apart from static mixing elements, specific dynamic mixing elements can also be used. Suitable static and dynamic mixing elements are known from the prior art.

As a rule, on an industrial scale, the continuous liquid phase isocyanate preparation is carried out in two stages. In this context, in general in the first stage, at maximum temperatures of 220° C., preferably maximum temperatures of 160° C., the carbamoyl chloride is formed from the amine and phosgene and the amine hydrochloride is formed from the amine and the hydrogen chloride split off. This first stage is highly exothermic. In the second stage, both the carbamoyl chloride is cleaved to give TDI and hydrogen chloride, and the amine hydrochloride is converted into the carbamoyl chloride. The second stage is as a rule carried out at temperatures of at least 90° C., preferably from 100° C. to 240° C.

After the phosgenation in step a), in which a crude toluene-diisocyanate is formed, the separating off and purification of the TDI formed in the phosgenation step is carried out in step b). This is preferably effected by first separating the reaction mixture of the phosgenation into a liquid product stream and a gaseous product stream in a manner known to the person skilled in the art. The liquid product stream, i.e. the crude toluene-diisocyanate, substantially contains TDI, the solvent and a small portion of unreacted phosgene. The gaseous product stream substantially comprises hydrogen chloride gas, stoichiometrically excess phosgene and minor amounts of solvent and inert gases, such as, for example, nitrogen and carbon monoxide. This gaseous product stream is fed to a further working up, where as a rule solvent, excess phosgene and the hydrogen chloride gas formed are separated off. The solvent and excess phosgene are fed back to the reaction for economic reasons. The hydrogen chloride can be fed to various possible uses such as, for example, an oxychlorination of ethylene to give ethylene dichloride or a recycling process which recycles chorine back into the isocyanate process. These recycling processes include catalytic oxidation of hydrogen chloride, for example, by the deacon process, electrolysis of gaseous hydrogen chloride and electrolysis of an aqueous solution of hydrogen chloride (hydrochloric acid). A process for catalytic oxidation by the Deacon process is known and described in, WO-A-04/14845 which is believed to correspond to U.S. Pat. No. 6,916,953, the disclosure of which is hereby incorporated by reference, and a process for gas phase electrolysis of hydrogen chloride is known and described in WO-A-97/24320, which is believed to correspond to U.S. Pat. No. 6,010,612, the disclosure of which is hereby incorporated by reference. An overview of electrochemical recycling processes is given in the article "Chlorine Regeneration from Anhydrous Hydrogen" by Dennie Turin Mah, published in "12th International Forum Electrolysis, in Chemical Industry—Clean and Efficient Processing Electrochemical Technology for Synthesis, Separation, Recycle and Environmental Improvement, Oct. 11-15, 1998, Sheraton Sand Key, Clearwater Beach, Fla.".

The liquid product stream, i.e. the crude toluene-diisocyanate, is then (in general) fed to a multi-stage working up by distillation in step b), with the still dissolved phosgene and the solvent being separated off successively.

The distillation of the crude toluene-diisocyanate in step b) can be carried out by generally known methods such as those described in, for example, in EP-A-1413571 which is believed to correspond to U.S. Pat. No. 7,108,770, the disclosure of which is hereby incorporated by reference, and US 2003/0230476 A1, the disclosure of which is hereby incorporated by reference. This distillation preferably occurs by one of the three variants described herein:

Variant 1:

Variant 1 is described in principle in Chem Systems' PERP Report for TDI/MDI (Chem Systems, Process Evaluation Research Planning TDI/MDI 98/99 S8, Tarrytown, N.Y., USA: Chem Systems 1999, pp 27-32), the disclosure of which is hereby incorporated by reference. In this variant, after distillation to separate off phosgene has occurred, the liquid reaction mixture still has a solvent content of greater than 50% by weight, and preferably 55 to 65% by weight. This mixture is fed to separating off the solvent, with a solvent-TDI mixture being distilled off in a solvent distillation column in a pre-evaporator, and a liquid bottom product of the pre-evaporator being fed to a further processing, the so-called working up of the residue. This liquid stream contains, in addition to 2 to 10% by weight of the solvent, approx. 5 to 25% by weight of the distillation residue. Solvent is distilled off in the solvent distillation column and fed back to the process. This distillation can be carried out in one or two stages as described in U.S. Pat. No. 6,803,438, the disclosure of which is hereby incorporated by reference. The bottom product of this solvent distillation still contains, in addition to TDI, from 15 to 25% by weight of solvent content. This stream is fed into a so-called intermediate column, in which residual solvent is distilled off, and the solvent-free bottom product is fed to a final column, which is operated under reduced pressure and delivers the purified marketable isocyanate TDI as the distillate. A residue-containing part stream from the bottom of the pure column is likewise fed to the separating off of residue. Alternatively, the tasks of the fine and pure distillation columns can be combined here as described in U.S. Published Patent Application 2003/0230476 A1, the disclosure of which is hereby incorporated by reference, in a dividing wall column, a stream of low-boiling components and solvent, a fraction of pure TDI and a product stream, as the bottom product, containing TDI and higher-boiling components being formed. The last product stream mentioned is in turn fed to a working up of the distillation residue.

Variant 2:

In contrast to variant 1, in this embodiment, after phosgene has been separated off by distillation, the liquid reaction mixture still contain a solvent content of less than 50% by weight. This mixture is fed to a pre-evaporator, from which a solvent-isocyanate mixture having a solvent content of less than 50% by weight is distilled off in a distillation column, preferably over the head. This distillation column corresponds to the fine column in Variant 1. The liquid bottom product from the pre-evaporator is fed to a further processing, i.e. the so-called working up of the residue. This liquid stream contains, in addition to 2 to 10% by weight of solvent, approx. 5 to 20% by weight of the distillation residue. The solvent-free bottom product of the intermediate column is fed into the final column, which is operated under reduced pressure and delivers the purified marketable isocyanate TDI as the distillate. A residue-containing part stream from the bottom of the final column is likewise fed to the separating off of the residue. Alternatively, the tasks of these intermediate and final distillation columns can be combined here, as described in EP 1413571 A1 which is believed to correspond to U.S. Pat. No. 7,108,770, the disclosure of which is hereby incorporated by reference, in a dividing wall column, a stream of low-boiling components and solvent, a fraction of pure TDI and a product stream, as the bottom product, containing TDI and higher-boiling components being obtained. The last product stream mentioned is in turn fed to a working up of the distillation residue.

Variant 3:

Variant 3 comprises the distillation sequences described in variants 2 and 1 as set forth above, but without the particular pre-evaporator mentioned, which feeds a liquid bottom product comprising approx. 5 to 20% by weight of distillation residue to a working up of the residue. In this case, the content of distillation residue in the distillation sequences described is co-fed via the liquid streams of material to the particular last TDI purification column. This process is likewise known in principle, as described in EP 1717223 A2, which is believed to correspond to U.S. Published Patent Application 2007/0015934, the disclosure of which is hereby incorporated by reference. In this case, the distillation residue (i.e. mixture containing toluene-diisocyanate and the distillation residue) is discharged completely to the working up of residue from the last distillation column.

All the known processes for purification of crude TDI by distillation in step b) have the common feature, however, that, in addition to the desired purified TDI from the distillation, a mixture containing toluene-diisocyanate and distillation residue is obtained, and that this mixture must be further treated.

The hydrolysis of the distillation residue in step c) is carried out by a procedure in which the mixture containing toluene-diisocyanate and the distillation residue is mixed continuously with water at a temperature of less than 230° C. under an absolute pressure of less than 30 mbar (preferably in a static or dynamic mixing unit, or by means of nozzles, perforated diaphragms, etc.) and is reacted at a temperature of less than 230° C. under an absolute pressure of less than 30 bar, in one or more tubular reactors which are connected in series, toluenediamine is obtained. In this context, the tubular reactors employed are operated without back-mixing and a uniform dwell time distribution is thus ensured.

The hydrolysis of the distillation residue is preferably carried out as follows:

The pre-evaporator bottom product formed in step b) as described in working up variants 1 and 2 above, preferably contains, in addition to TDI and the distillation residue of TDI, from 2.0 to 10% by weight of solvent. This stream is preferably fed over a distillation column with a circulatory evaporator in order to distill off the residual solvent, which can be fed back to the preparation of TDI. The TDI-residue mixture which remains is preferably passed over a further heat exchanger, preferably a falling film evaporator, in order to adjust the desired ratio of amounts of TDI and distillation residue.

If the mixture to be hydrolysed, which contains TDI and the distillation residue of TDI, from the distillation according to variant 3 is removed as a liquid stream from the last distillation column, the additional separating off of residual solvent as described above: is not necessary. The mixture containing toluene-diisocyanate and the distillation residue of TDI is then preferably conveyed directly by means of forced delivery pumps into the hydrolysis reactor, i.e. one or more tubular reactors connected in series.

Regardless of the distillation process employed in step b) and likewise regardless of the separating off of the solvent which may be necessary, the mixture which contains toluene-diisocyanate and the distillation residue of TDI, and which is introduced into the hydrolysis reactor in step c) preferably contains from 10 to 90% by weight, and preferably from 40 to 60% by weight of toluene-diisocyanate, based on 100% by weight of the mixture. The mixture which contains toluene-diisocyanate and the distillation residue of TDI, and which is introduced into the hydrolysis reactor in step c) likewise preferably contains less than 1% by weight of solvent, and preferably from 0.001 to 0.5% by weight of solvent.

At the same time, water (preferably after being preheated in a heat exchanger) is conveyed into the hydrolysis reactor. Preferably, in this context, the mixture containing toluene-diisocyanate and the distillation residue of TDI, and the water are employed in the weight ratio of from 0.1:1 to 1:1. The water preferably employed is fresh water, water which has been distilled off from step c), and/or water of reaction which has been formed in the hydrogenation of dinitrotoluene (DNT) and has been distilled off as described in, for example, EP 1484312 A 1 which is believed to correspond to U.S. Pat. No. 7,122,701, the disclosure of which is hereby incorporated by reference. It is also possible to employ steam. Usable synergies manifest themselves here in the integrated system of nitration of toluene, preparation of TDA, phosgenation of TDA, working up of MI and recycling of chlorine, in that purified water of reaction from the hydrogenation of DNT as disclosed in EP-A-236839 which is believed to correspond to U.S. Pat. No. 4,720,326, the disclosure of which is hereby incorporated by reference, can be employed for the hydrolysis.

It is preferred that the water employed in step c) additionally comprises one or more bases. Bases which are preferably employed are aqueous sodium or potassium hydroxide solution, meta-toluenediamine, ortho-toluenediamine, amine-containing residue from a toluenediamine pure distillation, ammonia or secondary compounds formed in the hydrogenation of dinitrotoluene such as, for example, toluidines, aminomethylcyclo-hexanes or diaminomethylcyclohexanes. The distillation residue conventionally contains small amounts of chlorinated inorganic compounds and/or organic compounds having concentrations of preferably less than 1.5% by weight of chlorine, based on 100% by weight of the mixture. These secondary components are substantially hydrogen chloride and side chain-chlorinated and nucleus-chlorinated isocyanates. In addition, traces of compounds such as aromatic isocyanide dichlorides can also occur. The origin of the chlorine in these side reactions is to be found in traces of chlorine in the phosgene employed or in side reactions of phosgene.

Preferably, the bases fed in with the water are employed in a stoichiometric excess with respect to the chlorine contained in the chlorinated inorganic compounds and/or organic compounds which are contained in the mixture containing toluene-diisocyanate and the distillation residue of TDI. On the one hand, the base serves to bond the chloride, and on the other hand the base acts as a hydrolysis catalyst, and thus allows relatively mild reaction conditions, which are to be classified as favorable with respect to energy consumption and apparatus requirements, particularly when compared with examples in the literature which have been carried out in the absence of bases such as described, for example, in U.S. Pat. No. 6,255,529 B1, the disclosure of which is hereby incorporated by reference.

The dwell time of the reaction in step c) is preferably up to 50 minutes, and more preferably from 2 to 40 minutes.

A reaction mixture containing water, toluenediamine, hydrolysis residue and where appropriate, for example, sodium salts such as sodium chloride and sodium carbonate, is preferably formed in the reaction in step c). Preferably, the reaction mixture emerging from the one tubular reactor or from the last of the tubular reactors connected in series employed in step c) is first expanded, after the service water has been preheated in a heat exchanged led in countercurrent, thus forming a liquid hydrolysis mixture and a gas mixture. The reaction gases formed can be fed to a suitable disposal, for example, a waste gas combustion installation, or can be released into the atmosphere after appropriate purification such as, for example, in active charcoal absorption towers.

The isolation of TDA by distillation from the hydrolysis mixture in step d) is preferably preceded by the separating off of water by distillation. However, the separating off of water and the isolation of TDA from the hydrolysis mixture can also be carried out in a common distillation step.

The distillation in step d) can be carried out in a separate sequence of distillation steps in which water is preferably first separated off, and then TDA is then isolated by distillation. However, the distillation in step d) can also be carried out in a distillation which is in any case present such as, for example in a distillation unit present in the preparation of TDA.

In a preferred embodiment, in step d) the excess water is first distilled off from the liquid hydrolysis mixture obtained. For this, the hydrolysis mixture is preferably fed to a dewatering column with a circulatory evaporator, and optionally, one or more post-evaporators for residual dewatering. Residual carbon dioxide which still remains is separated off over the head in this column. The water distilled off is condensed and partly introduced back into the column as a reflux, in order to retain any entrained TDA. The water reflux is led through a container which serves as a separating bottle in order to separate out any low-boiling amine components formed such as, for example, diaminomethylcyclohexane. Depending on the hydrolysis reaction procedure, the amine can be employed again as the base, or it can be combined together with the low-boiling components separated off in the TDA dewatering of the TDA operation in the isocyanate integrated system, for the purpose of disposal. The low-boiling components obtained in the dewatering stage of the hydrolysis can optionally be combined with other amine-containing residues in the isocyanate integrated system such as, for example, with the TDA residue from the removal of the TDA residue, for the purpose of utilization.

The purified stream of water which is generated in the dewatering column can be removed as waste water or can be at least partly recycled as hydrolysis water into the hydrolysis in step c).

In step d), toluenediamine is obtained by distillation from the hydrolysis mixture, which has preferably been dewatered beforehand, and is at least partly recycled into the reaction in step a). The distillation is preferably carried out in vacuo, i.e. under reduced pressure.

Preferably, a mixture containing from 70 to 90% by weight of TDA and from 30 to 10% by weight of the hydrolysis residue, based on 100% by weight of the mixture, is then conveyed at a temperature of from 180 to 220° C. into a distillation column (i.e. a TDA purification column), which preferably serves to purify the TDA obtained from the hydrogenation of DNT by distillation. The distillation column is preferably operated under an absolute pressure of less than 80 mbar. The distillation column can be operated with an external circulatory evaporator, which is supplied with high-pressure steam. The TDA is distilled off over the column head and, is at least partly introduced on to the column again as a reflux. The other part is fed to a TDA storage. In all cases, the TDA which formed by hydrolysis in step c) is at least partially subsequently recycled into the phosgenation of TDA in step a).

The hydrolysis residue which results from the distillation in step d) conventionally still contains from 5 to 20% by weight of TDA, based on 100% by weight of the mixture, and is preferably removed from the bottom of the TDA purification column. This hydrolysis residue is then preferably fed to a disposal, which preferably serves for thermal utilization within the isocyanate integrated system of nitration of toluene, preparation of TDA, phosgenation of TDA, working up of TDI and recycling of chlorine. Preferably, the residue components obtained in the context of the preparation of TDA and TDI, which are substantially based on liquid amine components, such as, for example, TDI hydrolysis residue or residue of the pure distillation of TDA, or secondary compounds formed in the hydrogenation of dinitrotoluene, such as, for example, toluidines, aminomethylcyclo-hexanes or diaminomethylcyclohexanes, and any ortho-TDA which has not been used, are fed together to a thermal utilization (e.g. by combustion and subsequent generation of steam or heating up of substance streams). Processes for the catalytic hydrogenation of dinitrotoluene to give TDA and subsequent purification thereof by distillation are known to the person skilled in the art and described in, for example, EP-A-223 035 and EP-A-1 602 640, which are believed to correspond to U.S. Pat. No. 4,792,626 and U.S. Published Patent Application 2005/0263385, respectively, the disclosures of which are hereby incorporated by reference. Therein lies an advantage of this hydrolysis process, since it thereby makes it possible that only the handling of one overall residue is necessary in the total production chain of TDA and TDI, which means a considerable simplification of the process in practice.

The advantages of the process according to the invention can be summarized as follows:

The production of waste products from the preparation of TDI is minimized.

The process according to the invention is simple and economical due to the working up of the TDI distillation residue in one or more simple tubular reactors which can be operated at low temperatures and pressure, and which therefore can also be operated advantageously in terms of safety.

Compared with other processes of the prior art which are employed industrially, on the one hand, the handling of solid on the solid distillation residue is omitted, and at the same time, the loss of product by combustion which must be accepted when handling solid is avoided.

Due to the preferred use of bases, the introduction of chlorine into the product is avoided. The use of bases, in principle, makes it possible to separate off residue-containing streams from various stages of the working up of TDI, so that an optimum yield is also rendered possible in this respect.

The following prophetic example further illustrates details for the process of this invention. The invention, which is set forth in the foregoing disclosure, is not to be limited either in spirit or scope by this example. Those skilled in the art will readily understand that known variations of the conditions of the following procedure(s) can be used. Unless otherwise noted, all temperatures are degrees Celsius.

EXAMPLES

TDI which is prepared by the phosgenation of TDA in o-dichlorobenzene (ODB) as the solvent is purified by distillation. For this, a liquid phase is obtained from a pre-evaporator stage of the solvent distillation, and this is combined with the bottom product of a TDI purification column, the so-called fine column. The two streams have the following composition:

Bottom product of the pre-evaporator: consists of m-TDI, TDI distillation residue, and o-dichlorobenzene.

Bottom product of the distillation column: consists of m-TDI, and TDI distillation residue.

The two streams are introduced at the head of a stripping column equipped with a steam-operated circulatory evaporator. In the column, residual ODB is separated off over the head and is fed back to the phosgenation of TDA. This stream of vapors which is separated off is composed of ODB and m-TDI. The bottom product removed from this column is solvent-free and is composed of m-TDI and TDI distillation residue. This stream is then transferred into a falling film evaporator which is operated under a vacuum and which further concentrates the residue in this mixture. TDI which is distilled off is fed back to the process, and the bottom product of the falling film evaporator which contains a mixture of TDI and TDI distillation residue is pumped to the residue hydrolysis reaction. A buffer container is available, into which the mixture containing TDI and the distillation residue can be placed briefly in the event of an interruption in operation, and then fed back to the hydrolysis process. Alternatively, the mixture of TDI and TDI distillation residue can be fed to a thermal utilization.

The mixture containing TDI and TDI distillation residue is pumped continuously by means of a piston membrane pump at 145° C. under 25 bar into the hydrolysis reactor. The hydrolysis reactor is a tubular reactor through which the mixture flows from the bottom upward to the top. The hydrolysis medium (water) is pumped into the reactor intake by means of a second piston pump and is combined with the mixture containing TDI and TDI distillation residue by means of a static mixing unit. The aqueous phase, which is likewise fed continuously under 25 bar at 210° C., represents a larger stream of material than the stream of the organic phase. The aqueous phase additionally contains sodium hydroxide in dissolved form. The hydrolysis reaction occurs under a regulated pressure of 25 bar, and a two-phase mixture which contains carbon dioxide, the hydrolysis product, TDA, water and a mixture of sodium chloride and sodium carbonate, which escapes from the reactor after expansion once the hydrolysis reaction is complete. The expansion is preceded by a heat exchanger, which is used to preheat the water fed into the reactor. The expansion takes place from 25 bar to approximately atmospheric pressure, and the reaction mixture is passed into an expansion container upstream of the dewatering column.

From this expansion container, a gaseous and a liquid stream are fed into the dewatering column, with gaseous product and the reaction mixture in liquid form entering the column under the given pressure and temperature conditions of 106° C./1,400 mbar absolute. The gaseous content is composed of water and carbon dioxide, while the liquid stream comprises water and TDA. The remainder of the liquid stream comprises the hydrolysis product and the inorganic contents previously mentioned.

Carbon dioxide and water are separated off from the bottom product of TDA and hydrolysis product. The bottom product from the dewatering column, after passing through the circulatory evaporator, contains-water, TDA and hydrolysis product with inorganic contents, under normal pressure at a temperature of 200° C. Residual water is removed with a downstream steam-operated tubular heat exchanger, and the mixture which remains is led into a vacuum column, in which separation of the hydrolysis product from TDA is carried out under an absolute pressure of 80 mbar at a column bottom temperature of 273° C.

Purified TDA is distilled off from the vacuum column and is fed back to the phosgenation. The hydrolysis product, as well as the bottom product which has a residual TDA content, can be fed to a thermal utilization.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of toluene-diisocyanate, which comprises
   a) reacting toluenediamine with phosgene to form crude toluene-diisocyanate,
   b) purifying the crude toluene-diisocyanate by distillation to form purified toluene-diisocyanate and a mixture comprising toluene-diisocyanate and the distillation residue of toluene diisocyanate,
   c) mixing said mixture comprising toluene-diisocyanate and the distillation residue of toluene diisocyanate continuously with water, and one or more bases which are selected from the group consisting of aqueous sodium hydroxide solution and aqueous potassium hydroxide solution, at a temperature of less than 230° C. under an absolute pressure of less than 30 bar, and allowing said mixture, water and one or more bases to react under said conditions in one or more tubular reactors connected in series, which are operated without back-mixing, to form toluenediamine,
   d) optionally, purifying said toluenediamine formed in step c), and
   e) recycling at least a portion of said toluenediamine into the reaction in step a).

2. The process of claim 1, in which said mixture comprising toluene-diisocyanate and the distillation residue of toluene-diisocyanate which is formed in step b) comprises from 10 to 90% by weight of toluene-diisocyanate, based on 100% by weight of the mixture.

3. The process of claim 1, in which said mixture comprising toluene-diisocyanate and the distillation residue of toluene-diisocyanate and said water are mixed in the weight ratio of from 0.1:1 to 1:1.

4. The process of claim 1, in which said mixture comprising toluene-diisocyanate and the distillation residue of toluene-diisocyanate additionally comprises chlorine in the form of one or more chlorinated inorganic compounds and/or one or more organic compounds, and said bases are employed in a stoichiometric excess with respect to the chlorine.

5. The process of claim 1, in which step c) forms a reaction mixture comprising water, toluenediamine, hydrolysis residue and, optionally, chloride salt, and in which said reaction mixture emerging from the one tubular reactor or from the last of the tubular reactors connected in series is first expanded, thereby forming a liquid hydrolysis mixture and a gas mixture.

6. The process of claim 5, additionally comprising distilling said liquid hydrolysis mixture to yield said toluenediamine.

7. The process of claim 6, in which said distillation is vacuum distillation.

8. The process of claim 6, additionally comprising distilling said liquid hydrolysis mixture to first remove the water, and further distilling to yield said toluenediamine.

9. The process of claim 7, additionally comprising recycling said water which is removed from the liquid hydrolysis mixture by distillation into step c).

10. The process of claim 6, in which the distillation of said liquid hydrolysis mixture additionally forms a mixture comprising toluenediamine and hydrolysis residue, and feeding said mixture comprising toluenediamine and hydrolysis residue, together with any residues containing toluenediamine which are formed in the catalytic hydrogenation of dinitrotoluene to toluenediamine, and/or by the working up by distillation, and/or with o-toluenediamine, to a common thermal utilization.

* * * * *